US010613250B2

(12) United States Patent
Prioul et al.

(10) Patent No.: US 10,613,250 B2
(45) Date of Patent: Apr. 7, 2020

(54) IN SITU STRESS PROPERTIES (71) Applicant: SCHLUMBERGER TECHNOLOGY CORPORATION, Sugar Land, TX (US)

(72) Inventors: Romain Prioul, Cambridge, MA (US); Safdar Abbas, Sugar Land, TX (US); Ridvan Akkurt, London (GB)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 362 days.

(21) Appl. No.: 15/501,866

(22) PCT Filed: Jul. 23, 2015

(86) PCT No.: PCT/US2015/041754
§ 371 (c)(1),
(2) Date: Feb. 6, 2017

(87) PCT Pub. No.: WO2016/022301
PCT Pub. Date: Feb. 11, 2016

(65) Prior Publication Data
US 2017/0235016 A1    Aug. 17, 2017

Related U.S. Application Data (60) Provisional application No. 62/032,971, filed on Aug. 4, 2014.

(51) Int. Cl.
G06G 7/48      (2006.01)
G01V 11/00     (2006.01)
(Continued)

(52) U.S. Cl.
CPC .......... G01V 11/002 (2013.01); E21B 49/005 (2013.01); E21B 49/006 (2013.01);
(Continued)

(58) Field of Classification Search
None
See application file for complete search history.

(56) References Cited

U.S. PATENT DOCUMENTS 4,594,691 A    6/1986 Kimball et al.
5,214,613 A    5/1993 Esmersoy
(Continued)

FOREIGN PATENT DOCUMENTS

WO    WO2013155125 A1    10/2013
WO    WO2014022757 A1    2/2014
(Continued)

OTHER PUBLICATIONS

Ramakrishna, Sandeep et al., "Mineralogy Porosity Fluid Property and Hydrocarbon Determination of Oil Reservoirs of the Green River Formation in the Uinta Basin", Jun. 2013, Petrophysics, vol. 54, No. 3. (Year: 2013).*
(Continued)

Primary Examiner — Cedric Johnson (57) ABSTRACT

Anisotropic elastic properties and subsequently in situ stress properties for a rock formation surrounding a wellbore are computed from rock physics and geomechanical models. Mineralogy data measured from DRIFTS on cuttings from the wellbore and rock physics and geomechanical models that have been log-calibrated in another wellbore are used in the computation. The method includes: (1) Defining and calibrating rock physics and geomechanical models using data from the first wellbore; (2) using DRIFTS analysis to measure mineralogy data on rock cuttings obtained through drilling operation in the second wellbore; and (3) using previously calibrated models to estimate in situ stress properties, including a stress index and the minimum principal stress magnitude.

28 Claims, 7 Drawing Sheets (51) Int. Cl.

| | |
|---|---|
| *G01N 33/24* | (2006.01) |
| *G01N 21/3563* | (2014.01) |
| *E21B 49/00* | (2006.01) |
| *G01N 29/07* | (2006.01) |
| *E21B 49/02* | (2006.01) |
| *G01N 29/04* | (2006.01) |
| *G01V 99/00* | (2009.01) |
| *G01N 21/35* | (2014.01) |
| *G01N 21/71* | (2006.01) |

(52) U.S. Cl.
CPC ......... *E21B 49/02* (2013.01); *G01N 21/3563* (2013.01); *G01N 29/04* (2013.01); *G01N 29/07* (2013.01); *G01N 33/24* (2013.01); *G01V 99/005* (2013.01); *G01N 21/718* (2013.01); *G01N 2021/3595* (2013.01); *G01N 2291/028* (2013.01); *G01N 2291/02827* (2013.01); *G01N 2291/105* (2013.01)

(56) References Cited

U.S. PATENT DOCUMENTS

| | | | |
|---|---|---|---|
| 5,808,963 | A | 9/1998 | Esmersoy |
| 6,714,480 | B2 | 3/2004 | Sinha et al. |
| 8,906,690 | B2 | 12/2014 | Pomerantz |
| 8,967,249 | B2 | 3/2015 | Akkurt et al. |
| 9,135,475 | B2 | 9/2015 | Lecerf et al. |
| 9,228,425 | B2 | 1/2016 | Ganguly et al. |
| 9,329,122 | B2 | 5/2016 | Herron et al. |
| 9,417,352 | B2 | 8/2016 | Sinha |
| 9,556,720 | B2 | 1/2017 | Onda et al. |
| 9,625,599 | B2 | 4/2017 | Prioul et al. |
| 9,659,252 | B2 | 5/2017 | Jocker et al. |
| 9,810,062 | B2 | 11/2017 | Akkurt et al. |
| 2003/0167835 | A1* | 9/2003 | Sinha ............ G01V 1/48 73/152.16 |
| 2006/0100837 | A1 | 5/2006 | Symington et al. |
| 2009/0210160 | A1 | 8/2009 | Suarez-Rivera et al. |
| 2010/0238764 | A1 | 9/2010 | Pistre et al. |
| 2011/0015907 | A1 | 1/2011 | Crawford et al. |
| 2012/0078600 | A1 | 3/2012 | Horne et al. |
| 2012/0150515 | A1 | 6/2012 | Hariharan et al. |
| 2013/0013209 | A1 | 1/2013 | Zhu et al. |
| 2013/0046469 | A1 | 2/2013 | Herron et al. |
| 2013/0269933 | A1 | 10/2013 | Pomerantz et al. |
| 2013/0270103 | A1 | 10/2013 | Akkurt et al. |
| 2013/0273661 | A1 | 10/2013 | Pomerantz |
| 2015/0012251 | A1 | 1/2015 | Horne et al. |
| 2016/0047207 | A1 | 2/2016 | Lecerf et al. |
| 2016/0084756 | A1 | 3/2016 | Herron et al. |
| 2016/0115771 | A1 | 4/2016 | Ganguly et al. |
| 2016/0138392 | A1 | 5/2016 | Pomerantz et al. |

FOREIGN PATENT DOCUMENTS

| | | |
|---|---|---|
| WO | WO2014179684 A2 | 11/2014 |
| WO | WO2014209854 A1 | 12/2014 |

OTHER PUBLICATIONS

Franquet, J.A. et al., "Integrated Acoustic, Mineralogy, and Geomechanics Characterization of the Huron Shale, Southern West Virginia, USA", Nov. 15-17, 2011, Canadian Unconventional Resources Conference, Society of Petroleum Engineers. (Year: 2011).*

Abousleiman, Younane et al., "GeoMechanics Field Characterization of the Two Prolific U.S. Mid-West Gas Plays with Advanced Wire-Line Logging Tools", Oct. 4-7, 2009, SPE Annual Technical Conference and Exhibition, Society of Petroleum Engineers. (Year: 2009).*

Bhargava, Suresh et al., "Characterization of Some Australian Oil Shale using Thermal, X-Ray, and IR Techniques", Dec. 13, 2004, Fuel 84. (Year: 2004).*

Ali, Anwar Husen Akbar et al., "Water Rocks Change—Mechanical Earth Modeling", 2003, Oilfield Review, 15(1). (Year: 2003).*

Nagy, Z.R. et al., "Interactive 3D Geomechanical Modeling to Determine Distribution and Impact of Stresses in Deepwater Gulf of Mexico Subsalt and Near-Salt Environments", Jun. 23-26, 2013, 47th US Rock Mechanics/Geomechanics Symposium, (Year: 2013).*

Shahri, Mojtaba et al., "Advanced Geomechanical Analysis of Wellbore Strengthening for Depleted Reservoir Drilling Applications", Mar. 4-6, 2014, IADC/SPE Drilling Conference and Exhibition. (Year: 2014).*

Qiuguo, Li et al. "3-D Geomechanical Modeling and Wellbore Stability Analysis in Abu Butabul Field", Nov. 11-14, 2012, Abu Dhabi International Petroleum Exhibition & Conference, Society of Petroleum Engineers. (Year: 2012).*

Backus, G. E., "Long-Wave Elastic Anisotropy Produced by Horizontal Layering", Journal of Geophysical Research, 1962, 67(11), pp. 4427-4440.

Horne, S. A "A statistical review of mudrock elastic anisotropy", Geophysical Prospecting, 2013, 61(4), pp. 817-826.

Pistre, V. et al., "A new modular sonic tool provides complete acoustic formation characterization", 75th Annual International Meeting, SEG Technical Program Expanded Abstracts, 2005, pp. 368-371.

Sayers, C. M., "The effect of kerogen on the elastic anisotropy of organic-rich shales", Geophysics, 2013, 78(2), pp. D65-D74.

Thomsen, L., "Weak elastic anisotropy", Geophysics, 1986, 51(1), pp. 1954-1966.

Tsvankin, I., "Elements of basic theory of anisotropic wave propagation", in Seismic Signatures and Analysis of Reflection Data in Anisotropic Media, 2001, Chapter 1, p. 1, vol. 29 . Elsevier Science Ltd, 2001.

Vernik, L. et al., "Elastic Anisotropy of Source Rocks: Implications for Hydrocarbon Generation and Primary Migration." AAPG Bulletin, 1996, 80(4), pp. 531-544.

Zhao, X. G. et al., "In-situ stress measurements and regional stress field assessment of the Beishan area, China", Engineering Geology, 2013, 163, pp. 26-40.

Schlumberger, "Sonic Scanner Acoustic Scanning Platform", 2018, [http://www.slb.com/services/characterization/geomechanics/wireline/sonic_scanner.aspx], accessed Aug. 1, 2018, 2 pages.

Schlumberger, "Litho Scanner High-Definition Spectroscopy Service", 2018, [http://www.slb.com/services/characterization/petrophysics/wireline/litho_scanner.aspx], accessed Aug. 1, 2018, 1 page.

* cited by examiner

IN SITU STRESS PROPERTIES

CROSS REFERENCE TO RELATED APPLICATIONS

This application claims priority to U.S. Provisional Patent Application No. 62/032,971, filed Aug. 4, 2014, the entire disclosure of which is hereby expressly incorporated by reference herein.

FIELD

The subject disclosure generally relates to the field of geosciences (or Earth science) and surface activities in the oil and gas industry. More particularly, the subject disclosure relates to using mineralogy data from a borehole and log-calibrated rock-physics and geomechanics models to compute the anisotropic elastic properties of rocks and subsequently in situ stress properties along a well.

BACKGROUND

Detailed knowledge of geological formation stresses is desirable in the hydrocarbon production business, because formation stresses can affect the planning of well stimulation treatments to enhance hydrocarbon recovery as well as provide predictions of sanding and wellbore stability. In addition, formation stress determinations can also prove useful in determining the long-term stability of the formation and thus the suitability of the formation as a repository for waste disposal. Accordingly, there is a growing demand in the industry for the estimations or determinations of formation stresses.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The subject disclosure relates to using mineralogy data measured from DRIFTS (Diffuse reflectance infrared Fourier transform spectroscopy) analysis on cuttings in well B based upon a rock-physics model that has been log-calibrated in well A to compute the anisotropic elastic properties of rocks and subsequently in situ stress properties from a geomechanical model. According to some embodiments of this disclosure, instead of DRIFTS analysis, another measurement technique is used that provides detailed mineralogy weight fraction, including kerogen, on the cuttings of well B. Throughout this description, such alternative measurement techniques can be substituted from any and all references to DRIFTS techniques. The described techniques involve two main processes: (1) defining and calibrating rock physics and geomechanical models using data from well A; and (2) measuring the mineralogy data on rock cuttings obtained through drilling operation in well B and using previous models to estimate in situ stress properties, most notably, a stress index and the minimum principal stress magnitude. Each process involves several sub-processes that are further described. The rock physics model used and the calibrated logic using well logs, or laboratory measurements on whole or side-cores obtained from the well A, are described below.

According to some embodiments, a method of determining subterranean stress properties during a drilling process is described. The method includes: calibrating one or more models using log data gathered from a subterranean rock formation surrounding a first wellbore (or laboratory measurements on core samples from the first wellbore); determining mineralogy data by applying a DRIFTS analysis process (or other measurements) on cuttings gathered during a drilling process of a second wellbore; and determining one or more stress properties of the subterranean rock formation surrounding the second wellbore based at least in part on application of the mineralogy data to the one or more calibrated models. According to some embodiments, the DRIFTS analysis and/or determining stress properties are performed after (rather than during) the drilling process. For example, cutting material may be stored for a long time after well B is drilled. In cases where the DRIFTS analysis and/or determining stress properties is performed after the drilling process, it can be done at the wellsite or in a location remote from the wellsite.

According to some embodiments, the one or calibrated models includes a rock physics model that relates mineralogy to elasticity, and wherein the determining of the one or more stress properties is based in part on applying the mineralogy data to the calibrated rock physics model to determine elasticity properties (such as elastic moduli). According to some embodiments, the one or more stress properties are determined in part by applying the determined elasticity properties to a geomechanical model that relates the elasticity to the one or more stress properties, such as minimum principal stress.

According to some embodiments, the DRIFTS analysis process on the cuttings from the second wellbore includes a determination of a subset of inorganic and organic mineralogy weight fractions using the DRIFTS analysis.

According to some embodiments, multipole sonic log data is gathered from the second borehole, and the rock physics model is calibrated using weight and elasticity data from both the first and second wellbores. According to some embodiments, the rock physics model relates mineralogy, porosity and fluid saturation to elasticity; also, the rock physics model is calibrated using mineralogy, porosity and fluid saturation data from the first wellbore. According to some embodiments, porosity data and fluid saturation data is available from the second wellbore and is also used to calibrate the rock physics model. In such cases the method can be used on conventional reservoirs as defined below.

As used herein "unconventional" reservoirs and/or resources generally refers to those petroleum reservoirs whose permeability/viscosity ratio uses technology to alter either the rock permeability or the fluid viscosity in order to produce the petroleum at commercially competitive rates. More specifically, as used herein, "unconventional" reservoirs refers to a reservoir with less than 0.1 mD permeability (so-called "tight") and with porosity of less than 10, with or without organic minerals such as gas shale, oil shale, oil-bearing shale, tight gas, tight oil, and organic-rich shale. In unconventional reservoirs, a further distinction is drawn herein between organic-rich and non-organic-rich mineral reservoirs. In the description, heavy oil and onshore viscous oil in high permeability reservoirs are not included.

As used herein "conventional" reservoirs and/or resources refers to those that can be produced commercially without altering permeability or viscosity. More specifically, as used herein, "conventional" reservoirs refers to a reservoir with greater than 0.1 mD permeability and with porosity of greater than 10.

According to some embodiments, the models calibrated using data from the first wellbore is further used for determining stress properties in other wells, such as third and fourth wellbores where the DRIFTS analysis is used on cuttings of each of the third and fourth wellbores.

According to some embodiments, a system for determining subterranean stress properties during a drilling process is described. The system includes a processing system programmed and configured to calibrate one or more models using log data gather from a subterranean rock formation surrounding a first wellbore; determine mineralogy data by applying a DRIFTS analysis process on cuttings gathered during (or after) a drilling process of a second wellbore; and determining one or more stress properties of the subterranean rock formation surrounding the second wellbore, based at least in part on the application of the mineralogy data to the one or more calibrated models.

According to some embodiments, Diffuse Reflectance Infrared Fourier Transform Spectroscopy (DRIFTS) can quickly measure mineralogy in sediments with minor sample preparation. According to some embodiments, DRIFTS analysis including sample preparation can be performed in less than 20 minutes for any mud type, which allows the technique to keep up with the drilling at the wellsite. As mentioned, supra, there are a number of alternative measurements options to DRIFTS measurements. Such alternatives include, for example, for unconventional organic-rich shale reservoirs: ATR (Attenuated total reflectance); LIBS (Laser-induced breakdown spectroscopy); FTIR (Fourier Transform Infrared)+LECO (LECO for TOC (total organic carbon)); XRF (X-Ray Fluorescence) RBF+LECO; and XRD (X-ray diffraction)+LECO. For non-organic-rich shale reservoirs LECO need not be used as there is no TOC, and example alternatives include: ATR; LIBS; FTIR; XRF RBF; and XRD. Additionally, according to some embodiments, combination of several measurements may be used instead of or in addition to DRIFTS measurement. Such combinations include: DRIFTS+ATR; DRIFTS+XRF; DRIFTS+XRD; XRD+XRF; and ATR+XRF. Throughout this description, such alternative measurements and combinations of measurements can be substituted from any and all references to DRIFTS techniques.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Following is a description of a method for determining stress properties of a rock mineralogy of interest. Using known spectroscopy measurement devices on rocks, one can measure the elemental yields and dry-weight fractions for Al, Ba, C, Ca, Cl, Cu, Fe, Gd, H, K, Mg, Mn, Na, Ni, O, S, Si, and Ti, for example. The dry-weight fractions of the elements can then be converted into dry-weight fractions of most common inorganic minerals, for example: quartz, calcite, dolomite, illite, smectite, kaolinite, chlorite, anhydrite, pyrite, coal, evaporite, siderite, etc. Moreover, recent modern spectroscopy tools (in the lab or in the field) can estimate dry-weight fractions of organic carbon content (referred as TOC: total organic carbon) from which dry-weight fractions of kerogen can be estimated.

Mineralogy from Cuttings Using DRIFTS Spectroscopy Measurement.

According to some embodiments, mineralogy data is measured using a spectroscopy tool on drillings cuttings. Several patents and patent publications are identified that are related to the application of DRIFTS to compute rock mineralogy on cuttings. U.S. Pat. Publ. No. 2013/0269933, discusses the cleaning and preparation procedure, using solvent cleaning. U.S. Pat. Publ. No. 2013/0046469, discusses a procedure to invert DRIFTS for mineralogy and TOC, using local calibration. U.S. Pat. Publ. No. 2013/0273661 discusses a procedure to invert DRIFTS for mineralogy, TOC, and maturity, without local calibration. U.S. Pat. No. 8,967,249 discusses using DRIFTS along with other wellsite measurements for formation evaluation. International Pat. Publ. No. WO2014/022757, discusses integrating DRIFTS with Raman spectroscopy. International Pat. Publ. No. WO 2014/179684 discusses combining DRIFTS plus Leco TOC to get maturity. International Pat. Publ. No. WO 2014/209854 discusses a method to quantify separately bitumen and kerogen by DRIFTS, for use in WBM wells in tight oil. Each of the above patents, patent publications and patent applications are incorporated herein by reference.

According to some embodiments, mineralogy logs from tools, such as Schlumberger's Litho Scanner Logging tool, are used for model calibration.

The following definition of elastic anisotropy and symmetries of interest are used herein. Following Tsvankin, Ilya. *Seismic signatures and analysis of reflection data in anisotropic media*. Chapter 1, Page 1. Vol. 29. Elsevier Science Ltd, 2001: "a medium (or a region of a continuum) is called anisotropic with respect to a certain parameter if this parameter changes with the direction of a measurement. If an elastic medium is anisotropic, seismic waves of a given type propagate in different directions with different velocities. This velocity anisotropy implies the existence of a certain structure (order) on the scale of seismic wavelength imposed by various physical phenomena."

Many sedimentary rocks exhibit elastic anisotropy that can be of intrinsic nature due to clay orientation and layering (e.g., shales) or can be induced by the presence of fractures or the stress sensitivity of the formation. The vast majority of existing studies of seismic anisotropy are performed for a transversely isotropic (TI with 5 elastic constants) medium, which has a single axis of rotational symmetry. However, some formations possess lower symmetries such as orthorhombic (9 elastic constants) or monoclinic (13 elastic constants) due, for instance, to the presence of fractures or stress-related anisotropy (the lowest symmetry being triclinic with 21 elastic constants). Elastic moduli are defined using the Voigt notation convention (by replacing each pair of indices, ij and kl, of the fourth-rank elastic tensor $C_{ijkl}$ by a single index according to the "Voigt recipes": $11 \rightarrow 1$, $22 \rightarrow 2$, $33 \rightarrow 3$, $23 \rightarrow 4$, $13 \rightarrow 5$, $12 \rightarrow 6$) and the density-normalized moduli $C_{ij}/\rho$ have units of velocity squared. As an example, we restrict our description to transversely isotropic (TI) media, described by five elastic constants, known as $C_{11}$, $C_{33}$, $C_{55}$, $C_{66}$, and $C_{13}$, for which the elastic stiffness tensor can be written as follows where $C_{12}=C_{11}-2C_{66}$:

$$C_{(TI)} = \begin{bmatrix} C_{11} & C_{12} & C_{13} & 0 & 0 & 0 \\ C_{12} & C_{11} & C_{13} & 0 & 0 & 0 \\ C_{13} & C_{13} & C_{33} & 0 & 0 & 0 \\ 0 & 0 & 0 & C_{55} & 0 & 0 \\ 0 & 0 & 0 & 0 & C_{55} & 0 \\ 0 & 0 & 0 & 0 & 0 & C_{66} \end{bmatrix}$$

When the three indexes 1, 2, and 3 of the fourth-rank elastic tensor $C_{ijkl}$ are defined respectively North, East, and Vertical directions, the previous TI medium is called Vertical Transverse Isotropy or VTI.

The first four of these five moduli are related to the squared speeds for wave propagation in the vertical and horizontal directions. The wavespeed for horizontally propagating compressional vibration is $V_{11}=\sqrt{(C_{11}/\rho)}$, the wavespeed for horizontally propagating shear vibration with horizontal polarization is $V_{12}=\sqrt{(C_{66}/\rho)}$, the wavespeed for vertically propagating shear vibration with horizontal polarization (and by symmetry horizontally propagating shear vibration with vertical polarization) is $V_{31}=V_{13}=\sqrt{(C_{55}/\rho)}$, and the wavespeed for vertically propagating compressional vibration is $V_{33}=\sqrt{(C_{33}/\rho)}$. The remaining parameter, $C_{13}$, cannot be estimated without either making off-axis measurements or invoking a physical or heuristic model with fewer than five parameters. We define slowness as the inverse of a velocity.

According to some embodiments, model calibration uses elastic anisotropy from a multipole sonic tool with at least monopole and dipole. In some embodiments, elastic anisotropy from Schlumberger's Sonic Scanner tool is used for model calibration. Presently, borehole sonic measurements to estimate slowness or velocity (and elastic stiffness) rely on axial wave propagation in fluid filled boreholes with transmitters and receivers distributed on a tool along the axis of the borehole, and wave propagation between them either in the formation or at the interface formation-borehole wall. Measurements from such sonic tools can accurately measure three or four available sonic slowness measurements, i.e., one compressional, one or two dipole shear, and one tube-wave related slowness. For a vertical well within a VTI medium, each sonic measurement can be uniquely related to one component of the stiffness tensor, i.e., the components $c_{33}$, $c_{55}$, and $c_{66}$ are related respectively to one compressional, one dipole shear, and one tube-wave shear slowness. In a horizontal well, the same is true for the compressional and the dipole shear slownesses, related respectively to $c_{11}$, $c_{55}$, and $c_{66}$. Such tools lack the direct measurements of two measurements of the five elastic TI constants, for example, $c_{11}$ and $c_{13}$ for vertical wells in VTI media and $c_{33}$ and $c_{13}$ for horizontal wells. Existing "axial" multimode sonic tool (monopole P- and S-waves, dipole flexural waves and monopole Stoneley) are described, for example, in the following references for Sonic Scanner: Pistre, et al, 2005, A new modular sonic tool provides complete acoustic formation characterization, 75th Annual International Meeting, SEG, Expanded Abstracts, 1-4; U.S. Pat. Nos. 4,594,691; 5,214,613; and 5,808,963, each of which are incorporated herein by reference. The one compressional and two shear slownesses are then used to extract the five transversely isotropic (TI) elastic moduli for examples using the following indirect techniques: U.S. Pat. No. 6,714,480; U.S. Pat. Publ. No. 2009/0210160; U.S. Pat. Publ. No. 2012/0078600; Int'l Pat. Publ. No. WO2013/016470; and Intl Pat. Publ. No. WO2013/112466, all of which are incorporated herein by reference. New techniques to determine several elastic constants including $C_{13}$ are also reported in: U.S. Pat. Publ. No. US 2014/0369165 and in U.S. patent application Ser. No. 14/108,64917, filed on Dec. 17, 2013, each of which are incorporated herein by reference. According to some embodiments, other petrophysical logs, such as the ones from conventional PEx platform (density and neutron logs), may be used in the calibration process.

Figure 1:
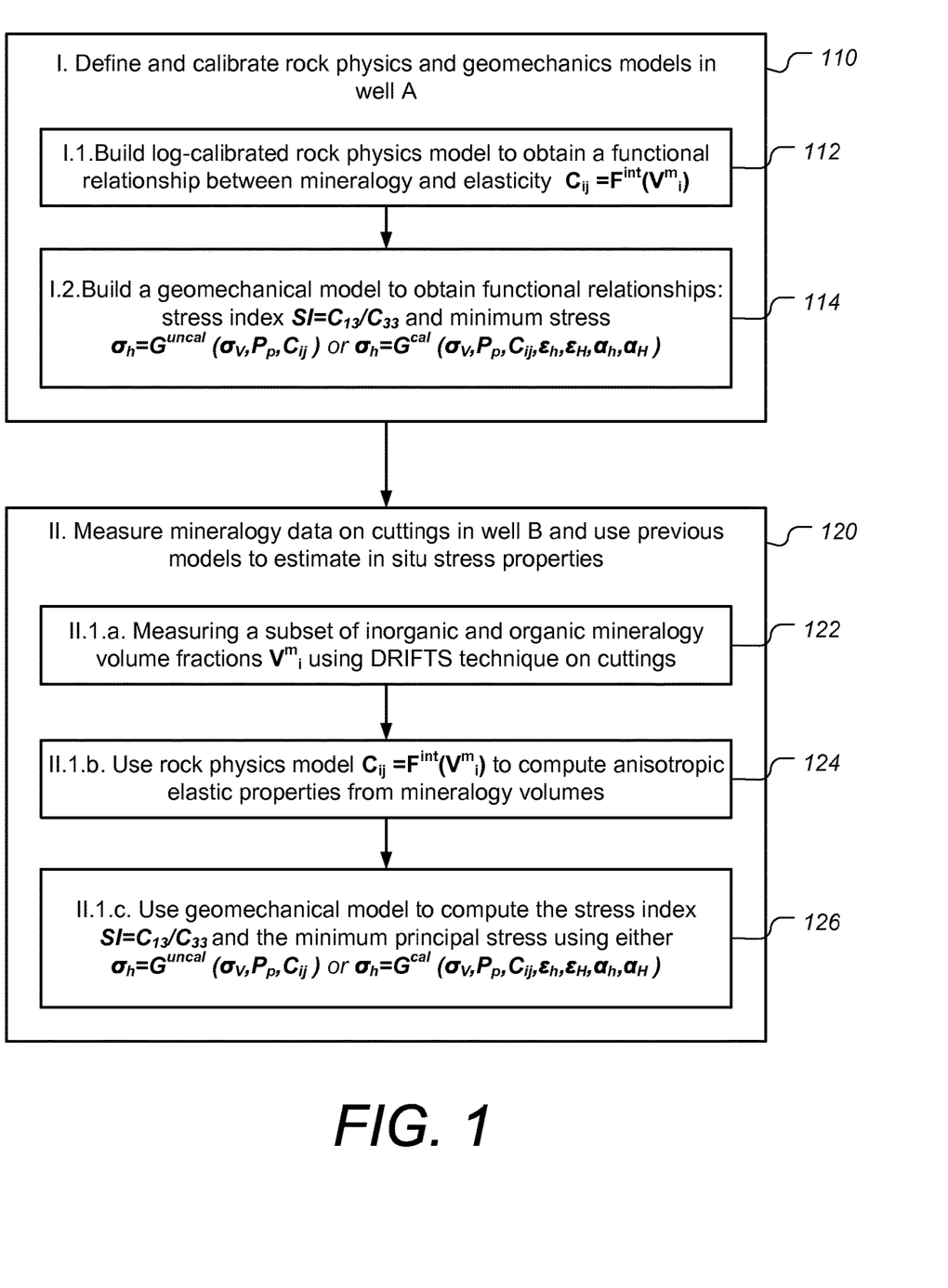
FIG. 1 depicts aspects of a process to calibrate models and apply these models, according to some embodiments.

According to some embodiments, in a given wellbore, mineralogy data is measured on cuttings along with a log-calibrated rock-physics model to compute the anisotropic elastic properties of rocks and subsequently in situ stress properties from a geomechanical model. FIG. 1 depicts aspects of a process to calibrate models and apply these models, according to some embodiments. In block 110 rock physics and geomechanics models are defined and calibrated in a given well A. In block 120, mineralogy data is measured on cuttings from well B, and the previous models are then used to estimate in situ stress properties. Block 110 includes block 112 in which a log-calibrated rock physics model is built to obtain a functional relationship between mineralogy and elasticity $C_{ij}=F^{int}(V^m_i)$. Block 110 also includes block 114 in which a geomechanical model is built to obtain functional relationships: stress index $$SI = \frac{C_{13}}{C_{33}}$$

and minimum stress $\sigma_h = G^{uncal}(\sigma_v, P_p, C_{ij})$ or $\sigma_h = G^{cal}(\sigma_v, P_p, C_{ij}, \alpha_h, \alpha_H, \epsilon_h, \epsilon_H)$. Block 120 includes blocks 122, 124 and 126. In block 122, a subset of inorganic and organic mineralogy volume fractions $V^m_i$ is measured using DRIFTS technique on cuttings. In block 124, the rock physics model $C_{ij} = F^{int}(V^m_i)$ is used to compute anisotropic elastic properties from mineralogy volumes. In block 126, the geomechanical model built in block 114 is used to compute the stress index $$SI = \frac{C_{13}}{C_{33}}$$

and the minimum principal stress using either $\sigma_h = G^{uncal}(\sigma_v, P_p, C_{ij})$ or $\sigma_h = G^{cal}(\sigma_v, P_p, C_{ij}, \alpha_h, \alpha_H, \epsilon_h, \epsilon_H)$.

Figure 2:
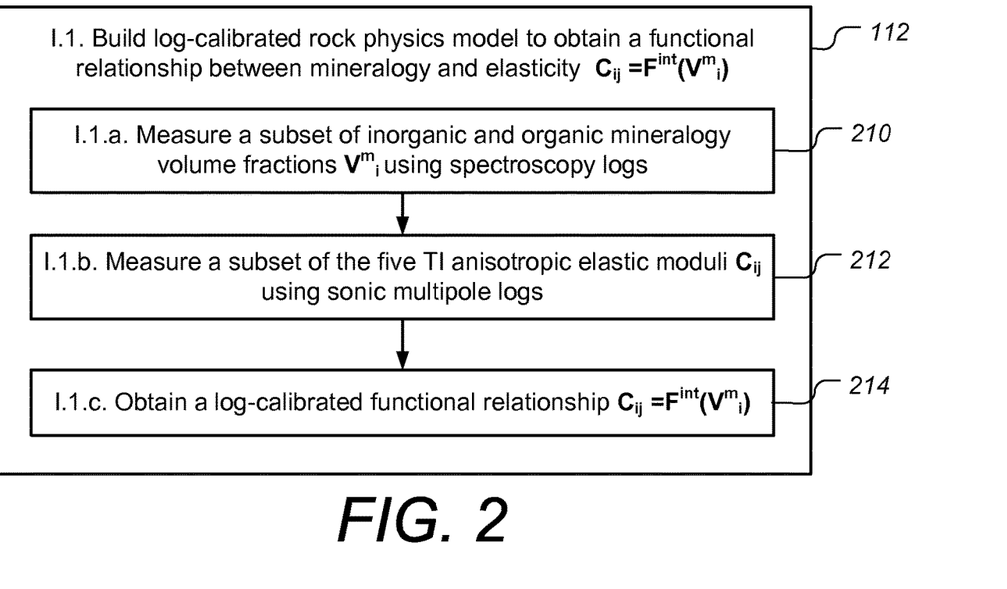
FIG. 2 depicts further details of building a log-calibrated rock physics model to obtain a function relationship between mineralogy and elasticity, according to some embodiments.

FIG. 2 depicts further details of building a log-calibrated rock physics model to obtain a function relationship between mineralogy and elasticity, according to some embodiments. In block 112 a log-calibrated rock physics model is built to relate mineralogy data to elasticity data, and this block further includes blocks 210, 212 and 214. As described, supra, as an alternative to using well logs from well A for calibration, one or more laboratory measurements on core samples from well A can be used. Accordingly, for any and all references herein to calibration using logs, it is understood that one or more laboratory core measurements could be used instead. According to some embodiments, measurements of elastic properties can be made on core samples from well A in the lab with ultrasonic transmitter-receiver devices. In block 210, subset of inorganic and organic mineralogy weight fractions are measured using spectroscopy logs. Schlumberger's Litho Scanner is an example of a tool that can be used to obtain a suitable spectroscopy log. Examples of the mineralogy weight fractions include: $W_i = \{W_{kerogen}, W_{quartz}, W_{calcite}, W_{dolomite}, W_{illite}, W_{smectite}, W_{kaolinite}, W_{chlorite}, W_{anhydrite}, W_{pyrite}, W_{coal}, W_{evaporite}, W_{siderite},$ etc. ...}. Volume fractions of matrix $V^m_i = \{V_{kerogen}, V_{quartz}, V_{calcite}, V_{dolomite}, V_{illite}, V_{smectite}, V_{kaolinite}, V_{chlorite}, V_{anhydrite}, V_{pyrite}, V_{coal}, V_{evaporite}, V_{siderite},$ etc. ...} where $\Sigma_i V^m_i = 1$ can be determined using independent knowledge of the mineral densities $\rho^m_i = \{\rho_{kerogen}, \rho_{quartz}, \rho_{calcite}, \rho_{dolomite}, \rho_{illite}, \rho_{smectite}, \rho_{kaolinite}, \rho_{chlorite}, \rho_{anhydrite}, \rho_{pyrite}, \rho_{coal}, \rho_{evaporite}, \rho_{siderite},$ etc. ...}. Note that further detail is given below on how to compute $V^m_i$, according to some embodiments.

According to some embodiments, if possible, using additional logs such as bulk density, neutron, and resistivity logs (e.g. PeX logs), volume fractions are estimated of the fluid-filled porous rock components. That is, some of $V^{rock}_i = \{V_{kerogen}, V_{quartz}, V_{calcite}, V_{dolomite}, V_{illite}, V_{smectite}, V_{kaolinite}, V_{chlorite}, V_{anhydrite}, V_{pyrite}, V_{coal}, V_{evaporite}, V_{siderite},$ etc. ...} and porosity $\phi$ (where $\Sigma_i V^{rock}_i + \phi = 1$) as well as fluid saturations $S_f = \{S_{water}, S_{oil}, S_{gas}\}$ and fluid densities $\rho f = \{\rho_{water}, \rho_{oil}, \rho_{gas}\}$ are estimated.

In block 212, a subset of the five TI anisotropic elastic moduli $C_{ij}$ are measured using sonic multipole logs, such as from Schlumberger's Sonic Scanner and bulk density log(s), i.e. some of $C_{ij} = \{C_{11}, C_{33}, C_{55}, C_{66}, C_{13}\}$, using known processing techniques. For example, $C_{33}$, $C_{55}$, and $C_{66}$ can be directly measured in a vertical well, and $C_{11}$ and $C_{13}$ inferred from the measurements and additional theoretical or empirical considerations.

In block 214, using data from blocks 210 and 212, the rock physics transform $C_{ij} = F^{int}(V^m_i)$ is built that uses the volume fractions of matrix minerals to compute several elastic moduli of an anisotropic VTI rock, in particular, $C_{33}$ and $C_{13}$. Note that further detail is given below on how to build and calibrate the model.

Figure 8:
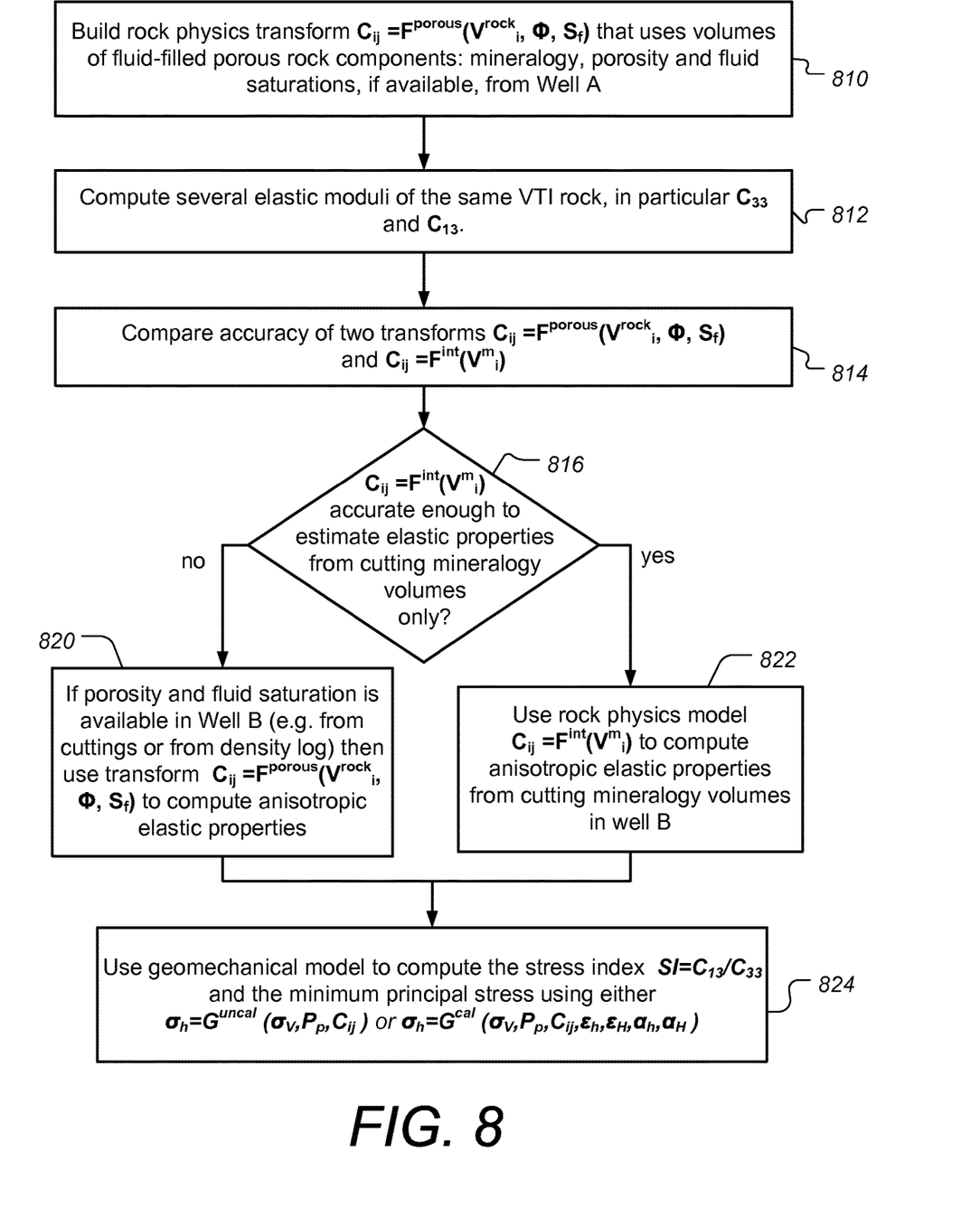
FIG. 8 depicts further detail of using an alternative rock physics transform in cases when porosity and fluid saturation data is available in the first well (well A), according to some embodiments.

According to some embodiments, if possible, another rock physics transform $C_{ij} = F^{porous}(V^{rock}_i, \phi, S_f)$ is built that uses the volume of fluid-filled porous rock components, porosity and fluid saturations to compute several elastic moduli of the same VTI rock, in particular, $C_{33}$ and $C_{13}$. FIG. 8 depicts further detail of using an alternative rock physics transform in cases when porosity and fluid saturation data is available in the first well (well A), according to some embodiments. In block 810, the alternate rock physics transform $F^{porous}(V^{rock}_i, \phi, S_f)$ is built when porosity and fluid saturation data is available in the first well (well A). In block 812, several elastic moduli of the same VTI rock are computed, in particular $C_{33}$ and $C_{13}$. In block 814, the accuracy of the two transforms $C_{ij} = F^{int}(V^m_i)$ and $C_{ij} = F^{porous}(V^{rock}_i, \phi, S_f)$ is compared and assessed to determine, in block 816, whether $C_{ij} = F^{int}(V^m_i)$ is accurate enough to estimate elastic properties from volume fractions of the matrix only. If $C_{ij} = F^{int}(V^m_i)$ is not accurate enough, in block 820 the transform $C_{ij} = F^{porous}(V^{rock}_i, \phi, S_f)$ is used to compute anisotropic elastic properties, assuming porosity and fluid saturation is available from Well B (e.g. from cuttings or from a density log). If $C_{ij} = F^{int}(V^m_i)$ is accurate enough, in block 822, then it is used to compute anisotropic elastic properties from cutting mineralogy volumes in Well B. In block 824, the geomechanical model is used to compute the stress index $$SI = \frac{C_{13}}{C_{33}}$$

and the minimum principal stress using either $\sigma_h = G^{uncal}(\sigma_v, P_p, C_{ij})$ or $\sigma_h = G^{cal}(\sigma_v, P_p, C_{ij}, \alpha_h, \alpha_H, \epsilon_h, \epsilon_H)$.

Figure 3:
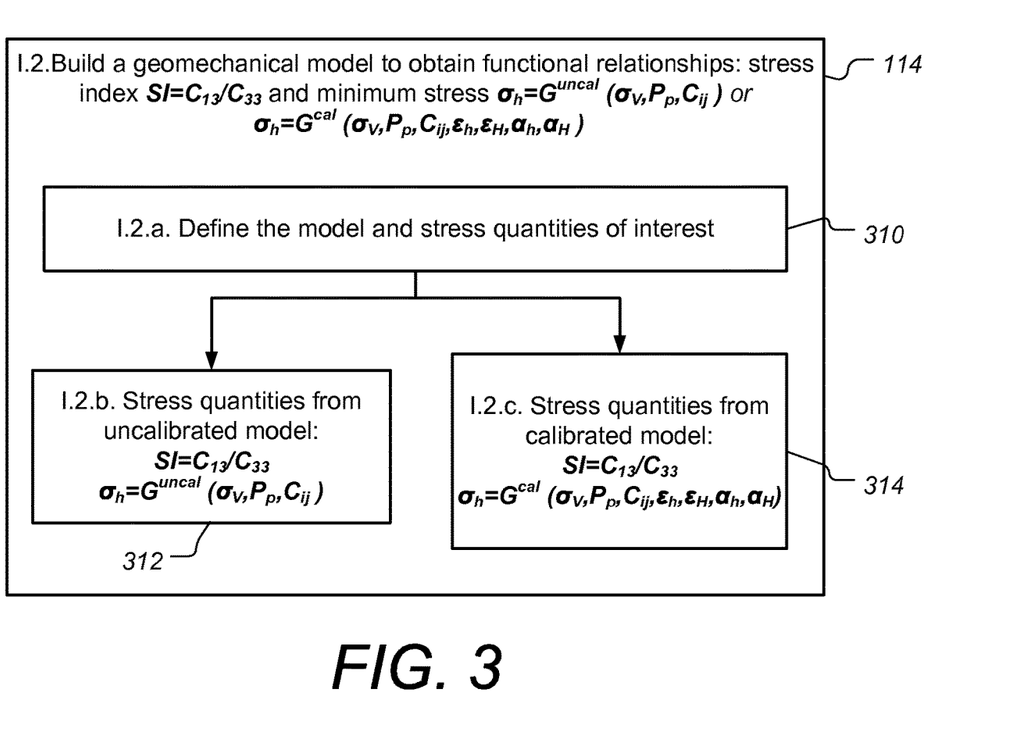
FIG. 3 depicts further detail of building a geomechanical model that relates the minimum principal stress magnitude to anisotropic elastic data, bulk density and additional quantities defined by the model, according to some embodiments.

FIG. 3 depicts further detail of building a geomechanical model that relates the minimum principal stress magnitude to anisotropic elastic data, bulk density and additional quantities defined by the model, according to some embodiments. Block 114 includes blocks 310, 312 and 314 as shown. In block 310, the model and stress quantities of interest are defined. For example, we can define a geomechanics transform from theoretical considerations such that the minimum principal stress magnitude is a function, $\sigma_h = G(\sigma_v, P_p, C_{ij}, \alpha_h, \alpha_H, \epsilon_h, \epsilon_H)$, of the vertical principal stress $\sigma_v$, the pore pressure $P_p$, the rock properties (elasticity $C_{ij}$ and Biot-Willis coefficients an and ail) and additional strains $\epsilon_h$ and $\epsilon_H$ as follows:

$$\sigma_h = \frac{C_{13}}{C_{33}}(\sigma_V - \alpha_V P_p) + \alpha_h P_p + \left(C_{11} - \frac{C_{13}^2}{C_{33}}\right)\epsilon_h + \left(C_{12} - \frac{C_{13}C_{23}}{C_{33}}\right)\epsilon_H$$

In block 312, stress quantities are from an uncalibrated geomechanics model. In general, the vertical stress at a given depth, z, is known from the integration of the bulk density, $\sigma_v = \int_0^z g\rho_b dz$ and the pore pressure from local knowledge. In cases where the local strains ($\epsilon_h$ and $\epsilon_H$) and Biot-Willlis coefficients ($\alpha_h$ and $\alpha_H$) are unknown, we can assume $\epsilon_h = \epsilon_H = 0$ and $\alpha_h = \alpha_H = 1$, and provide the uncalibrated quantities:

A stress index, SI, defined as $$SI = \frac{C_{13}}{C_{33}},$$

The minimum principal stress as $$\sigma_h = \frac{C_{13}}{C_{33}}(\sigma_V - P_p) + P_p$$

In block 314, stress quantities are from a calibrated model. In cases where hydraulic measurements of $\sigma_h$ (such as from Schlumberger's MDT tool for micro-fracturing tests) are available in well A, the local strains ($\epsilon_h$ and $\epsilon_H$) can be estimated. If core samples are available in well A from laboratory testing, Biot-Willlis coefficients $\alpha_h$ and $\alpha_H$ can be estimated. In such, we have a calibrated geomechanics model that can used to compute the following quantities:

A stress index, SI, defined as $$SI = \frac{C_{13}}{C_{33}},$$

The minimum principal stress as $$\sigma_h = \frac{C_{13}}{C_{33}}(\sigma_V - \alpha_V P_p) + \alpha_h P_p + \left(C_{11} - \frac{C_{13}^2}{C_{33}}\right)\epsilon_h + \left(C_{12} - \frac{C_{13}C_{23}}{C_{33}}\right)\epsilon_H$$

Figure 4:
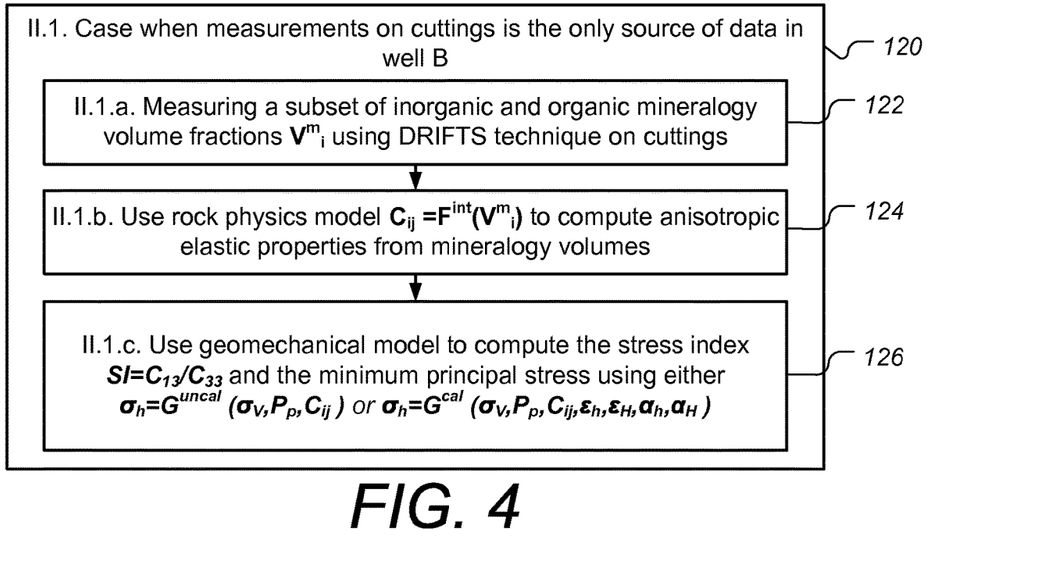
FIG. 4 depicts measuring mineralogy data on cuttings in a second well and using previous models to estimate in situ stress properties, according to some embodiments.

FIG. 4 depicts further detail measuring mineralogy data on cuttings in a second well and using previous models to estimate in situ stress properties, according to some embodiments. Block 120 illustrates a case when measurements on cuttings from the second well (well B) are the source of data, and other data from the second well, such as sonic log data, is either not available or not relied upon. In block 122 a subset of inorganic and organic mineralogy weight fractions are measured using DRIFTS technique on cuttings. That is, some of $W_i = \{W_{kerogen}, W_{quartz}, W_{calcite}, W_{dolomite}, W_{illite}, W_{smectite}, W_{kaolinite}, W_{chlorite}, W_{anhydrite}, W_{pyrite}, W_{coal}, W_{evaporite}, W_{siderite}, \text{etc.} \ldots\}$ are measured. Volume fractions of matrix $V^m_i = \{V_{kerogen}, V_{quartz}, V_{calcite}, V_{dolomite}, V_{illite}, V_{smectite}, V_{kaolinite}, V_{chlorite}, V_{anhydrite}, V_{pyrite}, V_{coal}, V_{evaporite}, V_{siderite}, \text{etc.} \ldots\}$ where $\Sigma_i V^m_i = 1$ are determined using independent knowledge of the mineral densities $\rho^m_i = \{\rho_{kerogen}, \rho_{quartz}, \rho_{calcite}, \rho_{dolomite}, \rho_{illite}, \rho_{smectite}, \rho_{kaolinite}, \rho_{chlorite}, \rho_{anhydrite}, \rho_{pyrite}, \rho_{coal}, \rho_{evaporite}, \rho_{siderite}, \text{etc.} \ldots\}$.

In block 124, the rock physics model $C_{ij} = F^{int}(V^m_i)$ from block 214 is used to compute anisotropic elastic properties from mineralogy volume. According to some embodiments, in cases when porosity and fluid saturations are also available in the second well (well B), the rock physics model $C_{ij} = F^{porous}(V^{rock}_i, \phi, S_f)$ can be used to compute anisotropic elastic properties from mineralogy volume, porosity and fluid saturations. This is shown in block 820 of FIG. 8. In some cases, porosity and fluid saturation can be available from drilling cuttings from the second well (well B). In other cases, porosity and fluid saturation can be available from a density log from either a nuclear wireline tool or a while-drilling tool from the second well (well B). According to some embodiments, the use of rock physics transform $C_{ij} = F^{porous}(V^{rock}_i, \phi, S_f)$ is used with porosity and fluid saturation from the second well is suitable for reservoirs having higher porosity than "conventional" reservoirs.

Referring again to FIG. 4, in block 126, the geomechanical model from block 114 is used to compute the stress index, $$SI = \frac{C_{13}}{C_{33}},$$

and minimum principal stress using either the uncalibrated model $\sigma_h = G^{uncal}(\sigma_v, P_p, C_{ij})$ from block 312 or calibrated model $\sigma_h = G^{cal}(\sigma_v, P_p, C_{ij}, \alpha_h, \alpha_H, \epsilon_h, \epsilon_H)$ from block 314, where vertical stress and pore pressure are calculated at the given depth using locally known gradients.

Figure 5:
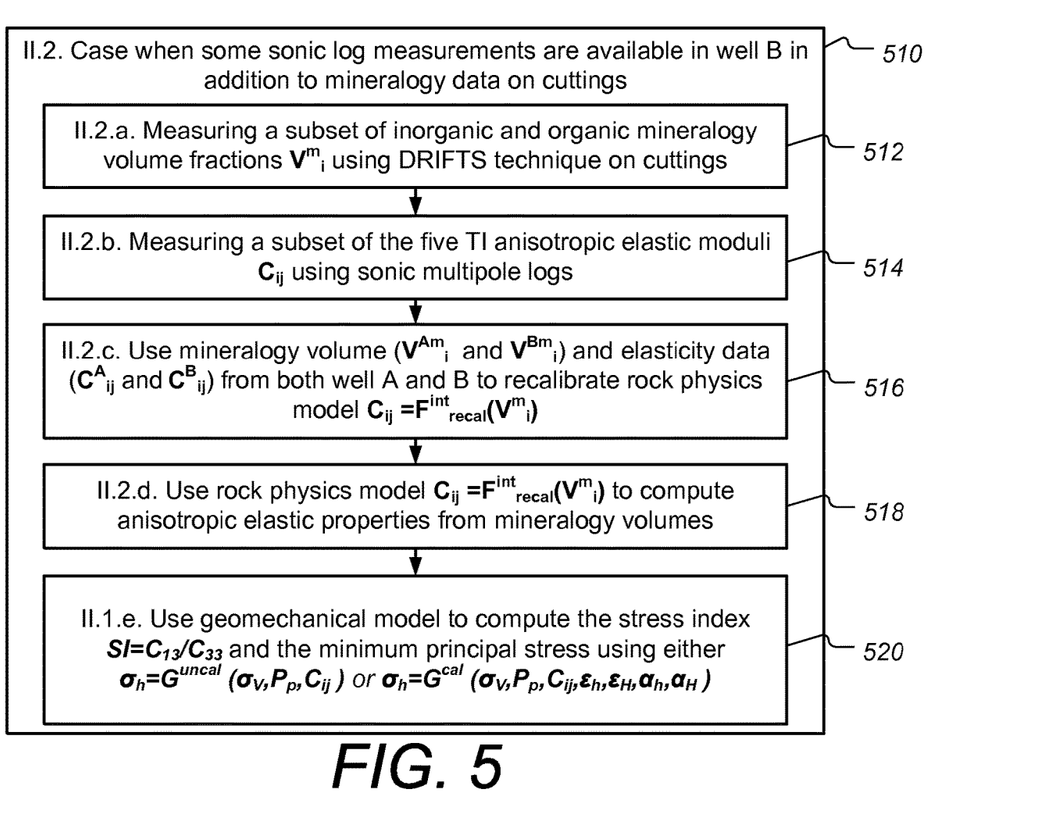
FIG. 5 depicts measuring mineralogy data on cuttings and sonic logs in a second well and using previous models to estimate in situ stress properties, according to some embodiments.

FIG. 5 depicts further detail measuring mineralogy data on cuttings in a second well and using previous models to estimate in situ stress properties, according to some embodiments. Block 510 illustrates a case when some sonic log measurements are available in the second well (well B), in addition to mineralogy data on cuttings. In block 512, a subset of inorganic and organic mineralogy weight fractions using DRIFTS technique on cuttings. That is, some of $W_i = \{W_{kerogen}, W_{quartz}, W_{calcite}, W_{dolomite}, W_{illite}, W_{smectite}, W_{kaolinite}, W_{chlorite}, W_{anhydrite}, W_{pyrite}, W_{coal}, W_{evaporite}, W_{siderite}, \text{etc.} \ldots\}$ are measured. Volume fractions of matrix $V^m_i = \{V_{kerogen}, V_{quartz}, V_{calcite}, V_{dolomite}, V_{illite}, V_{smectite}, V_{kaolinite}, V_{chlorite}, V_{anhydrite}, V_{pyrite}, V_{coal}, V_{evaporite}, V_{siderite}, \text{etc.} \ldots\}$ are determined, where $\Sigma_i V^m_i = 1$ using independent knowledge of the mineral densities $\rho^m_i = \{\rho_{kerogen}, \rho_{quartz}, \rho_{calcite}, \rho_{dolomite}, \rho_{illite}, \rho_{smectite}, \rho_{kaolinite}, \rho_{chlorite}, \rho_{anhydrite}, \rho_{pyrite}, \rho_{coal}, \rho_{evaporite}, \rho_{siderite}, \text{etc.} \ldots\}$.

In block 514, a subset of the five TI anisotropic elastic moduli $C_{ij}$ are measured using sonic multipole log data (such as from Schlumberger's Sonic Scanner tool). A bulk density log, i.e. some of $C_{ij} = \{C_{11}, C_{33}, C_{55}, C_{66}, C_{13}\}$, is obtained using known processing techniques. For example, $C_{11}$, $C_{55}$, and $C_{66}$ can be directly measured in a horizontal well. In block 516, mineralogy volumes ($V^{Am}_i$ and $V^{Bm}_i$) and elasticity data ($C^A_{ij}$ and $C^B_{ij}$) from both well A and B are used to recalibrate rock physics model $C_{ij} = F^{int}_{recal}(V^m_i)$. In block 518, the rock physics model $C_{ij} = F^{int}_{recal}(V^m_i)$ is used to compute anisotropic elastic properties from mineralogy volume. In block 520, the geomechanical model from block 114 is used to compute the stress index, SI, and the minimum principal stress using either the uncalibrated model $\sigma_h = G^{uncal}(\sigma_v, P_p, C_{ij})$ from block 312 or calibrated model $\sigma_h = G^{cal}(\sigma_v, P_p, C_{ij}, \alpha_h, \alpha_H, \epsilon_h, \epsilon_H)$ from block 314 where vertical stress and pore pressure are calculated at the given depth using locally known gradients.

According to some embodiments, the mineralogy data and stress properties generated in the processes described herein can be then used to compute reservoir quality (RQ) and completion quality (CQ) indexes as an input to hydraulic fracturing design software. See, U.S. Pat. Publ. No. 2012/0185225, and U.S. Pat. Publ. No. 2012-0179444, both of which are incorporated herein by reference.

According to some embodiments, further details of certain aspects of the above described processes will be given. When calculating mineralogy volume fractions $V^m_i$ from mineralogy weight fractions $W_i$ (e.g. from logs or DRIFTS on cuttings), such as described in blocks 122, 210, and 512, according to some embodiments, the following can used. Once the mineralogy weight fractions have been measured with either spectroscopy logs or DRIFTS on cuttings $W_i = \{W_{kerogen}, W_{quartz}, W_{calcite}, W_{dolomite}, W_{illite}, W_{smectite}, W_{kaolinite}, W_{chlorite}, W_{anhydrite}, W_{pyrite}, W_{coal}, W_{evaporite}, W_{siderite},$ etc. ... $\}$, the volume fractions of matrix $V^m_i = \{V_{kerogen}, V_{quartz}, V_{calcite}, V_{dolomite}, V_{illite}, V_{smectite}, V_{kaolinite}, V_{chlorite}, V_{anhydrite}, V_{pyrite}, V_{coal}, V_{evaporite}, V_{siderite},$ etc. ... $\}$ where $\Sigma_i V^m_i = 1$ can be computed using independent knowledge of the mineral densities $\rho^m_i = \{\rho_{kerogen}, \rho_{quartz}, \rho_{calcite}, \rho_{dolomite}, \rho_{illite}, \rho_{smectite}, \rho_{kaolinite}, \rho_{chlorite}, \rho_{anhydrite}, \rho_{pyrite}, \rho_{coal}, \rho_{evaporite}, \rho_{siderite},$ etc. ... $\}$ and computed matrix density $\rho^{matrix}$ (including organic and inorganic), as follows: $V^m_i = W_i / \rho^m_i * \rho^{matrix}$.

In defining and calibrating rock physics transform $C_{ij} = F^{int}(V^m_i)$, such as described in blocks 112, 214, 516, the following calibration technique can be used. The rock physics model can be based upon different effective medium elastic theories. The elastic behavior of a layered medium, with the axis of symmetry perpendicular to the layers (VTI as described herein), is described in Backus, George E. "Long-Wave Elastic Anisotropy Produced by Horizontal Layering." *Journal of Geophysical Research* 67, no. 11 (1962): 4427-4440 (hereinafter "Backus (1962)") through a long-wave equivalent of the original medium. Each layer may be considered as isotropic or transversely isotropic, but the effective medium will behave as transversely isotropic. Shales are composed of inorganic minerals and organic matter (kerogen). Fluids are trapped in the system of pores in the minerals and kerogen. The constituent minerals and kerogen are considered as isotropic. The stiffness matrix for an isotropic material depends upon two constants e.g. the stiffness matrix for an isotropic material can be expressed in terms of the bulk modulus K and the shear modulus pt as follows:

$$C_{ij} = \begin{bmatrix} K+4\mu/3 & K-2\mu/3 & K-2\mu/3 & 0 & 0 & 0 \\ K-2\mu/3 & K+4\mu/3 & K-2\mu/3 & 0 & 0 & 0 \\ K-2\mu/3 & K-2\mu/3 & K+4\mu/3 & 0 & 0 & 0 \\ 0 & 0 & 0 & \mu & 0 & 0 \\ 0 & 0 & 0 & 0 & \mu & 0 \\ 0 & 0 & 0 & 0 & 0 & \mu \end{bmatrix} \quad (1)$$

The effective medium elastic coefficient $C_{33}$ is given by Backus (1962) as the Reuss average of the individual components:

$$C_{33} = \langle c_{33}^{-1} \rangle^{-1} = 1/\Sigma_{i=1}^M V^m_i / c^i_{33} \quad (2)$$

where $c_{33}$ denotes the elastic coefficient of an individual component of the rock composition and the brackets $\langle . \rangle$ denote the volume weighted average of the quantity inside using the volume $V^m_i$ obtained from the M mineralogy measurements. As each individual component is considered as isotropic, the individual coefficient $c^i_{33}$ is given by (1) as:

$$c^i_{33} = K^i + 4\mu^i/3 \quad (3)$$

Typical values for the bulk modulus K and shear modulus μ of common minerals is given in Mavko et. al (2003). Value of K and μ for the kerogen can be obtained from: Vernik, Lev, and Charles Landis. "Elastic Anisotropy of Source Rocks: Implications for Hydrocarbon Generation and Primary Migration." *AAPG Bulletin* 80, no. 4 (1996): 531-544 (hereinafter "Vernik and Landis (1996)"). Similarly, the effective medium elastic coefficient μ is given by Backus (1962) as the Reuss average of the individual coefficients:

$$C_{55} = \langle c_{55}^{-1} \rangle^{-1} = 1/\Sigma V^m_i / c^i_{55} \quad (4)$$

where $c^i_{55} = \mu^i$ for each component of the rock matrix. The estimates for the $C_{33}$ coefficients and $C_{55}$ from the Backus (1962) averaging conforms well to the experimental results, as shown by Vernik and Landis (1996), these estimates are used in the model. On the other hand, the estimates for the coefficients $C_{11}$ and $C_{66}$ from the Backus (1962) averaging do not conform well to the experimental data. See, Sayers, Colin M. "The effect of kerogen on the elastic anisotropy of organic-rich shales." *Geophysics* 78, no. 2 (2013): D65-D74 (hereinafter "Sayers 2013"). The alternate relationship given by Vernik and Landis (1996) to compute these coefficients from individual components is $$c_{11} = \alpha M + (1-\alpha)N \quad (5)$$

$$C_{66} = \alpha P + (1-\alpha)Q \quad (6)$$

where $$M = \langle c_{11} \rangle + \langle c_{33}^{-1} c_{13} \rangle^2 \langle c_{33}^{-1} \rangle^{-1} - \langle c_{33}^{-1} c_{13}^2 \rangle \quad (7)$$

$$N = \langle c_{11}^{-1} \rangle^{-1} = 1/\Sigma_{i=1}^M V^m_i / c^i_{11} \quad (8)$$

$$P = \langle c_{66} \rangle = \Sigma_{i=1}^M V^m_i / c^i_{66} \quad (9)$$

and $$Q = \langle c_{66}^{-1} \rangle^{-1} = 1/\Sigma_{i=1}^M V^m_i / c^i_{66} \quad (10)$$

where $$c^i_{11} = K^i + 4\mu^i/3 \quad (11)$$

$$c^i_{13} = K^i + 2\mu^i/3 \quad (12)$$

$$c^i_{66} = \mu^i \quad (13)$$

for each mineral and kerogen. This results in a better conformance of the modeled elastic coefficients to the data as shown by Vernik and Landis (1996), provided the parameter a is estimated for the given dataset. For $C_{13}$, we have used the MANNIE model (U.S. Pat. Publ. No. 2009/0210160 A1, which is incorporated by reference herein), whereby the authors gave the following relationship between $C_{12}$ and $C_{13}$ $$C_{13} = \xi C_{12} \quad (14)$$

where the parameter $\xi = 0.79$ is given in Horne, S. A. "A statistical review of mudrock elastic anisotropy." *Geophysical Prospecting* 61, no. 4 (2013): 817-826 (hereinafter "Horne (2013)").

The strength of anisotropy in a TI medium can also be expressed in terms of three dimensionless parameters ($\epsilon$, $\gamma$ and $\delta$) known as the Thomsen parameters (See, Thomsen, L., 1986, Weak elastic anisotropy: Geophysics, 51, 1954-1966, which is incorporated herein by reference)

$$\epsilon = \frac{C_{11} - C_{33}}{2C_{33}} \quad (15)$$

$$\gamma = \frac{C_{66} - C_{55}}{2C_{55}} \quad (16)$$

$$\delta = \frac{(C_{13} + C_{55})^2 - (C_{33} - C_{55})^2}{2C_{33}(C_{33} - C_{55})} \quad (17)$$

Figure 6:
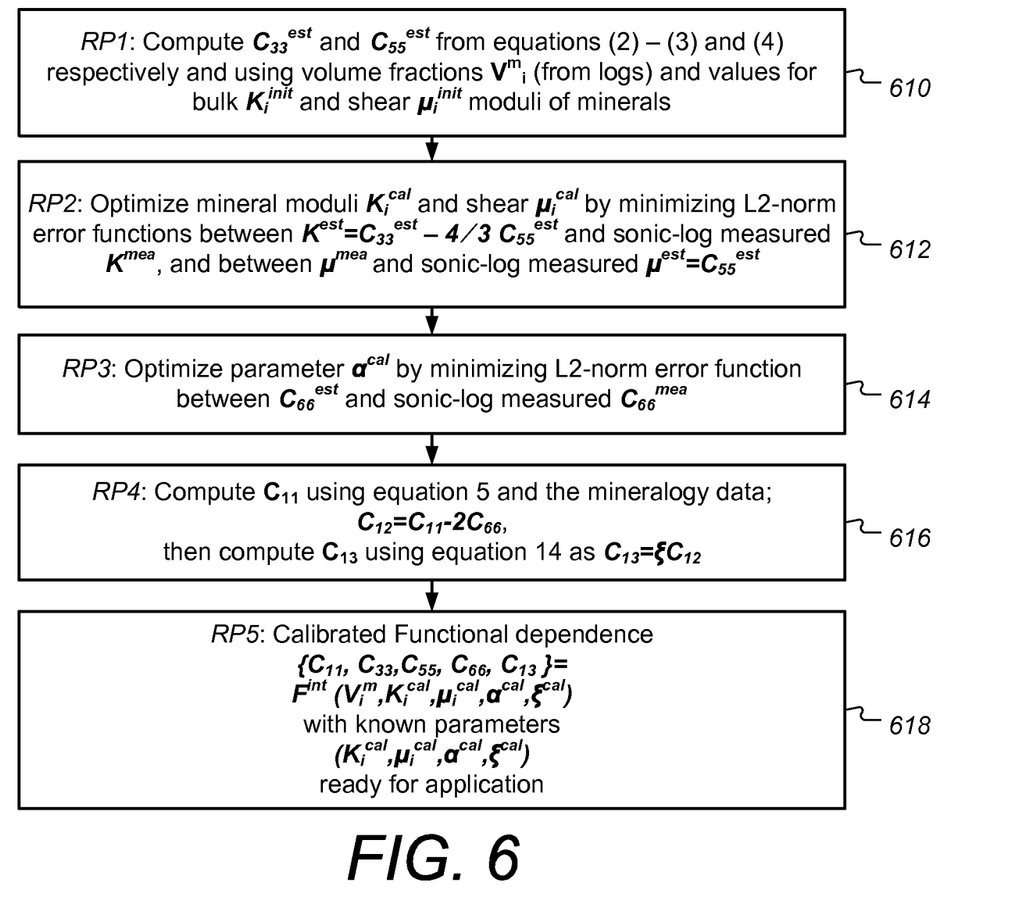
FIG. 6 illustrates further detail for defining and calibrating the rock physics transform $C_{ij}=F^{int}(V^m{}_i)$, according to some embodiments.

FIG. 6 illustrates further detail for defining and calibrating the rock physics transform $C_{ij} = F^{int}(V^m_i)$, according to some embodiments. In block 610, (Process RP1), the measured mineralogy volume fractions, $V^m_i$, measured from spectroscopy logs and values for bulk modulus $K^{init}_i$ and shear modulus $\mu^{init}_i$ of common minerals are first used to compute $C_{33}^{est}$ from equations (2) and (3), as well as $C_{55}^{est}$ from equation (4). We first visually compare the computed $K^{est} = C_{33}^{est} - 4/3\, C_{55}^{est}$ and $\mu^{est} = C_{55}^{est}$ to the same sonic-log measured quantities $K^{mea} = C_{33}^{mea} - 4/3\, C_{55}^{mea}$ and $\mu^{mea} = C_{55}^{mea}$.

Figure 7:
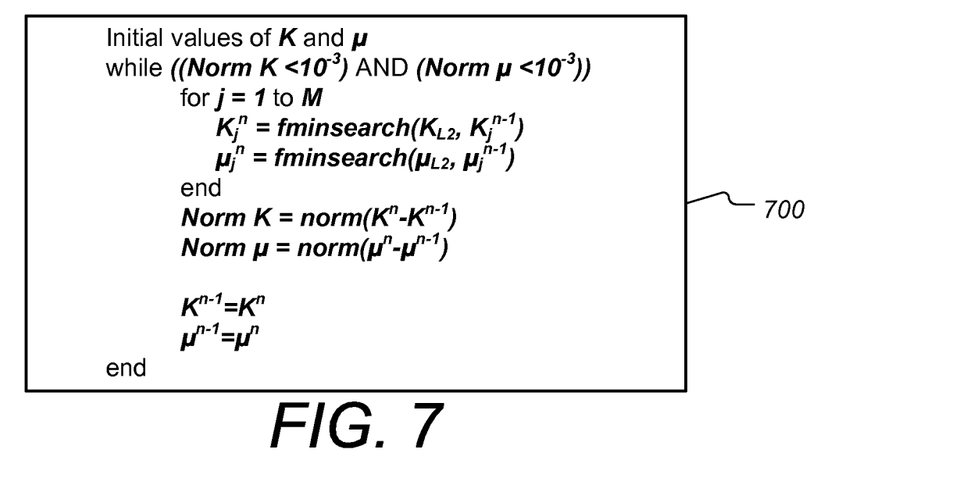
FIG. 7 is a diagram showing an optimization algorithm, according to some embodiments.

In block 612 (Process RP2), the bulk modulus $K_i$ and shear modulus $\mu_i$ of each mineral are optimized in order to match the local field conditions by iteratively minimizing an L2-norm cost function defined as follows $\mathrm{Err}_{L_2} = \sqrt{\sum_{i=1}^{N}(X_i^{est} - X_i^{mea})^2 / \sum_{i=1}^{N}(X_i^{mea})^2}$ where $X_i^{est}$ denotes the estimated value of quantity X, and $X_i^{mea}$ denotes the measured value of X at a data point i and N denotes the number of data points. According to some embodiments, an unconstrained optimization using fminsearch function in MATLAB to minimize the error in the $L_2$ norm for $K_i$ and $\mu_i$ can be used. FIG. 7 is a diagram showing an optimization algorithm, according to some embodiments. There are two loops in the algorithm 700. The outer loop checks for the convergence in K and $\mu$ values. The inner loop finds the value of K and $\mu$ that minimizes the $L_2$-norm for each component of the rock matrix. Here M is the total number of rock matrix components. The output of this process is a collection of mineral bulk $K_i^{cal}$ and shear $\mu_i^{cal}$ modulus that is locally calibrated for the given well to provide the link between elastic constants $C_{33}$ and $C_{55}$ and mineralogy.

In block 614 (process RP3), the measured mineralogy volume fractions, $V^m_i$, measured from spectroscopy logs and the optimized $K_i$ and $\mu_i$ from the previous process, are used to compute $C_{66}^{est}$ from equation (6) for a given parameter a, and then optimize a by minimizing the L2-norm $\mathrm{Err}_{L_2} = \sqrt{\sum_{i=1}^{N}(C_{66i}^{est} - C_{66i}^{mea})^2 / \sum_{i=1}^{N}(C_{66i}^{mea})^2}$. The output of this process is a value of $\alpha^{cal}$ that is locally calibrated for the given well to provide the link between elastic constants $C_{66}$ and mineralogy.

In block 616 (process RP4), knowledge of $\alpha^{cal}$ allows the computation of $C_{11}$ using equation (5) and the mineralogy data, and consequently, $C_{12} = C_{11} - 2C_{66}$. We then compute $C_{13}$ using equation (14), $C_{13} = \xi C_{12}$ where the parameter is taken as $\xi = 0.79$. Parameter $\xi^{cal}$ can be also locally calibrated on a field basis using laboratory dataset in the same or nearby well of the same formation.

In block 618, (process RP5), the complete model can be described by the functional dependence $\{C_{11}, C_{33}, C_{55}, C_{66}, C_{13}\} = F^{int}(V_i^m, K_i^{cal}, \mu_i^{cal}, \alpha^{cal}, \xi^{cal})$ where all parameters $(K_i^{cal}, \mu_i^{cal}, \alpha_i^{cal}, \tau^{cal})$ are known at the end of the calibration process in well A. Throughout this description (e.g. blocks 112, 124, 214, 516 and 518), this function is referred as $C_{ij} = F^{int}(V_i^m)$.

Figure 9:
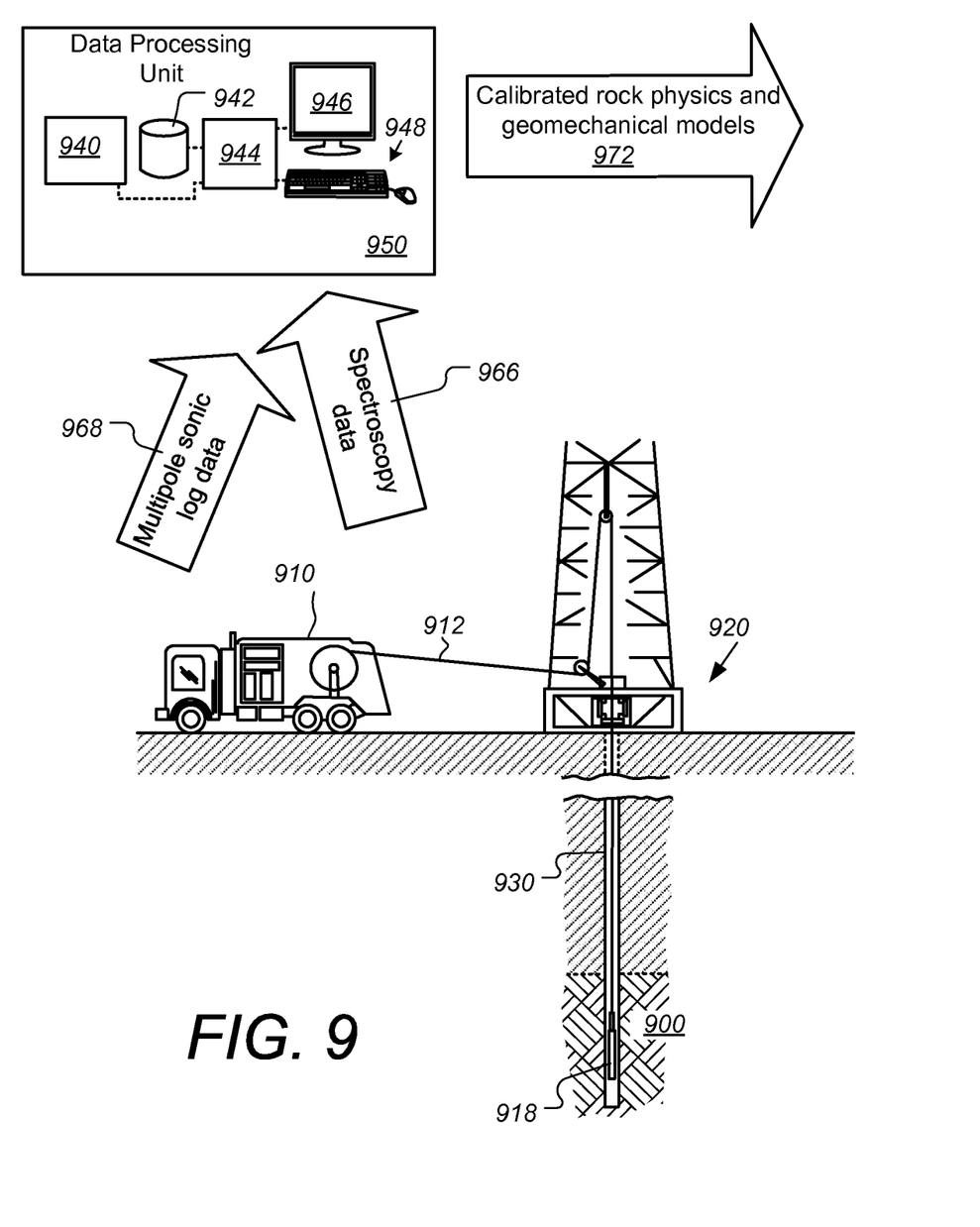
FIG. 9 is a diagram showing a wireline tool being deployed in a first wellbore along with a DRIFTS spectrometer and processing unit for defining and calibrating rock physics and geomechanical models, according to some embodiments.

FIG. 9 is a diagram showing a wireline tool being deployed in a first wellbore along with a DRIFTS spectrometer and processing unit for defining and calibrating rock physics and geomechanical models, according to some embodiments. Wireline truck 910 is deploying wireline cable 912 into first well 930 (also referred to herein as "well A") via wellsite 920. Wireline tool 918 is disposed on the end of the cable 912 in a subterranean rock formation 900. According to some embodiments, formation 900 is an unconventional reservoir, supra. Tool 918, according to some embodiments is a spectroscopy tool such as Schlumberger's Litho Scanner High-definition Spectroscopy tool. According to some embodiments, other wireline tools such as a multipole sonic tool can also be included on the tool string at the end of wireline cable 912. According to some embodiments, on a separate logging procedure a multipole sonic tool is run in well 930 using truck 910. According to some embodiments, the multipole sonic tool is Schlumberger's Sonic Scanner Acoustic Scanning Tool. Data from the tool 918 from rock formation 900 are retrieved at the surface in logging truck 910.

According to some embodiments, the spectroscopy data 966 is processed in a data processing unit 950, which can be located in the logging truck 910 or at some other location at wellsite 920. According to some embodiments, data processing unit 950 is located at one or more locations remote from the wellsite 920. The processing unit 950 includes one or more central processing units 944, storage system 942, communications and input/output modules 940, a user display 946 and a user input system 948. Data processing unit 950 can be used for carrying out the processing activity described in many of the figures referred to herein. Using the spectroscopy data 966 and sonic data 968, processing unit 950 can define and calibrate the rock physics and geomechanics models 972 such as described in FIGS. 1-3, 6 and 8.

Figure 10:
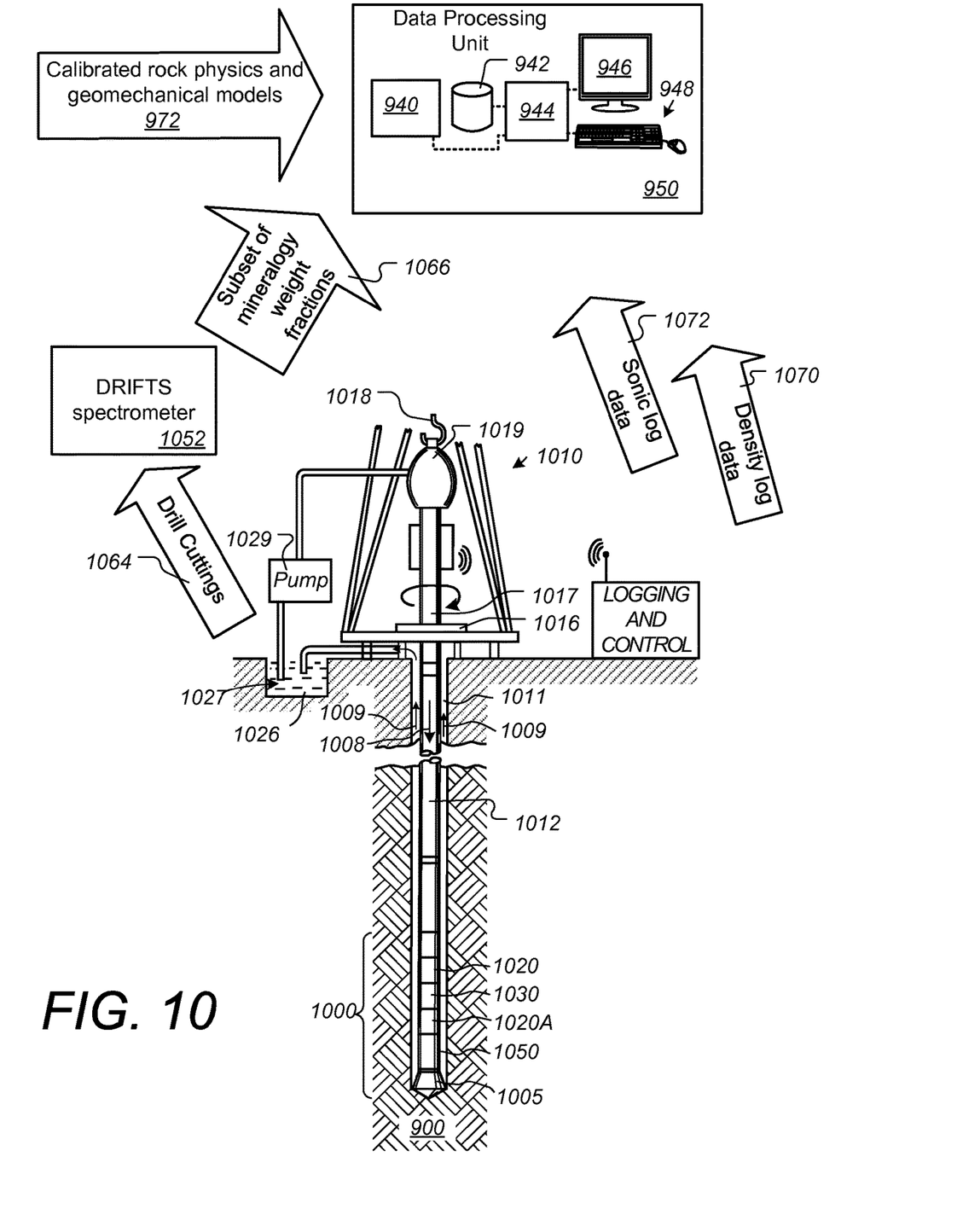
FIG. 10 illustrates a wellsite system in which mineralogy data is measured on a second well and by using rock physics and geomechanical models in situ stress for the second well can be estimated, according to some embodiments.

FIG. 10 illustrates a wellsite system in which mineralogy data is measured on a second well and by using rock physics and geomechanical models in situ stress for the second well can be estimated, according to some embodiments. The wellsite can be onshore or offshore. In this system, a second well 1011 (also referred to herein as "well B") is formed in subsurface formations by rotary drilling in a manner that is well known. Embodiments of the invention can also use directional drilling.

A drill string 1012 is suspended within the borehole 1011 and has a bottom hole assembly 1000 that includes a drill bit 1005 at its lower end. The surface system includes platform and derrick assembly 1010 positioned over the borehole 1011, the assembly 1010 including a rotary table 1016, kelly 1017, hook 1018 and rotary swivel 1019. The drill string 1012 is rotated by the rotary table 1016, energized by means not shown, which engages the kelly 1017 at the upper end of the drill string. The drill string 1012 is suspended from a hook 1018, attached to a traveling block (also not shown), through the kelly 1017 and a rotary swivel 1019, which permits rotation of the drill string relative to the hook. As is well known, a top drive system could alternatively be used.

In the example of this embodiment, the surface system further includes drilling fluid or mud 1026, stored in a pit 1027 formed at the well site. A pump 1029 delivers the drilling fluid 1026 to the interior of the drill string 1012 via a port in the swivel 1019, causing the drilling fluid to flow downwardly through the drill string 1012, as indicated by the directional arrow 1008. The drilling fluid exits the drill string 1012 via ports in the drill bit 1005, and then circulates upwardly through the annulus region between the outside of the drill string and the wall of the borehole, as indicated by the directional arrows 1009. In this well-known manner, the drilling fluid lubricates the drill bit 1005 and carries formation cuttings up to the surface as it is returned to the pit 1027 for recirculation.

The bottom hole assembly 1000 of the illustrated embodiment contains a logging-while-drilling (LWD) module 1020, a measuring-while-drilling (MWD) module 1030, a rotary-steerable system and motor, and drill bit 1005.

The LWD module 1020 is housed in a special type of drill collar, as is known in the art, and can contain one or a plurality of known types of logging tools. It will also be understood that more than one LWD and/or MWD module can be employed, e.g. as represented at 1020A. (References throughout, to a module at the position of 1020, can alternatively mean a module at the position of 1020A as well.) The LWD module includes capabilities for measuring, processing, and storing information, as well as for communicating with the surface equipment. In the present embodiment, the LWD module includes a resistivity measuring device as well as a number of other devices, such as a neutron-density measuring device, and a multipole sonic measuring device.

The MWD module 1030 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

According to some embodiments, drill cuttings 1064 are taken from the drilling mud, cleaned and analyzed using DRIFTS spectrometer 1052. DRIFTS spectrometer 1052 receives drill cuttings 1064. After sample preparation (e.g. washing and/or particle size modification) the DRIFTS spectrometer generates mineralogy data 1066 that is processed and interpreted in processing unit 950. According to some embodiments, data 1066 is a subset of mineralogy weight fractions and according to other embodiments, data 1066 are volume fractions which are derived from the weight fractions as described herein. Processing unit 950 uses the calibrated rock physics and geomechanical models 972 to generate an estimate of in situ stress in well 1011 (well B). According to some embodiments, if available, LWD module 1020 includes tools such nuclear density tool and/or a multipole sonic tool from which density log data 1070 and sonic log data 1072 can be obtained for use by processing unit 950 in estimating in situ stress in well 1011 (well B). According to some embodiments, processes as shown in block 120 of FIG. 1 and in FIGS. 4 and 5 are carried out while drilling.

Some of the methods and processes described above can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of determining subterranean properties comprising:
   i) providing a rock physics model and a geomechanical model, wherein the rock physics model relates mineralogy data to at least one elasticity property, wherein the geomechanical model relates at least one elasticity property to minimum principal stress magnitude, and wherein at least the rock physics model is calibrated using measurements of a subterranean rock formation surrounding a first wellbore;
   ii) determining mineralogy data by applying a mineralogy measurement process on cuttings gathered during a drilling process of a second wellbore;
   iii) determining at least one elasticity property of the subterranean rock formation surrounding the second wellbore based at least in part on application of the mineralogy data determined in ii) to the rock physics model of i); and iv) determining a minimum principal stress magnitude of the subterranean rock formation surrounding the second wellbore based at least in part on application of the at least one elasticity property determined in iii) to the geomechanical model of i).

2. The method according to claim 1 wherein the rock physics model of i) relates mineralogy data to elastic moduli, and wherein the at least one elasticity property determined in iii) comprises elastic moduli of the subterranean rock formation surrounding the second wellbore.

3. The method according to claim 1 wherein the measurements of the subterranean rock formation surrounding the first wellbore of i) includes spectroscopy log data and multipole sonic log data obtained from the first wellbore, and wherein the rock physics model of i) is calibrated by:
    determining a subset of inorganic and organic mineralogy volume fractions using the spectroscopy log data; and
    determining a subset of a plurality of anisotropic elastic moduli using the multipole sonic log data.

4. The method according to claim 3 wherein the inorganic and organic mineralogy volume fractions are determined using knowledge of mineral densities and measurements of inorganic and organic mineralogy weight fractions.

5. The method according to claim 3 wherein the anisotropic elastic moduli are transversely isotropic.

6. The method according to claim 1 wherein the measurements of the subterranean rock formation surrounding the first wellbore of i) include mineralogy measurements and acoustic measurements made in a lab on core samples gathered from the first wellbore, and wherein the rock physics model of i) is calibrated by:
    determining a subset of inorganic and organic mineralogy volume fractions using a mineralogy laboratory measurement device; and
    determining a subset of a plurality of anisotropic elastic moduli using an acoustic laboratory measurement device.

7. The method according to claim 1 wherein the geomechanical model of i) relates at least one elasticity property to uncalibrated minimum principal stress magnitude.

8. The method according to claim 1 wherein the geomechanical model of i) relates at least one elasticity property to minimum principal stress magnitude that is calibrated using the data gathered from the first wellbore.

9. The method according to claim 1 wherein the rock physics model of i) relates mineralogy data to elastic moduli C13 and C33, the geomechanical model of i) relates a ratio of the two elastic moduli C13 and C33 to a stress index, the at least one elasticity property determined in iii) includes the elastic moduli C13 and C33 of the subterranean rock formation surrounding the second wellbore, and the method further includes (v) determining a stress index of the subterranean rock formation surrounding the second wellbore based at least in part on application of the elastic moduli C13 and C33 determined in iii) to the geomechanical model of i).

10. The method according to claim 1 wherein the mineralogy measurement process of ii) is a Diffuse reflectance infrared Fourier transform spectroscopy (DRIFTS) analysis process performed on cuttings from the second wellbore, and the determining of the mineralogy data of ii) includes determining a subset of inorganic and organic mineralogy volume fractions using the DRIFTS analysis.

11. The method according to claim 1 wherein the mineralogy measurement process of ii) is of a type selected from or is a combination of one or more types selected from a group consisting of: Diffuse reflectance infrared Fourier transform spectroscopy (DRIFTS); Attenuated total reflectance (ATR); Laser-induced breakdown spectroscopy (LIBS); Fourier Transform Infrared (FTIR); FTIR+Laboratory Equipment Corporation method of estimating total organic carbon (LECO); X-Ray Fluorescence (XRF) Radial Basis Function (RBF); XRF RBF+LECO; X-ray diffraction (XRD); and XRD+LECO.

12. The method according to claim 11 further comprising receiving multipole sonic log data gathered from the second wellbore and wherein the rock physics model of i) is calibrated using volume data and elasticity data from both the first and second wellbores.

13. The method according to claim 12 wherein the volume data is acquired using knowledge of mineral densities and measurements of weight fractions from the first and second wellbores.

14. The method according to claim 1 wherein the rock physics model of i) relates mineralogy data, porosity data and fluid saturation data to at least one elasticity property, the rock physics model of i) being calibrated using mineralogy data, porosity data and fluid saturation data from the first wellbore.

15. The method according to claim 14 wherein porosity data and fluid saturation data from the second wellbore is available, and the determining of the at least one elasticity property of iii) is based in part on applying the mineralogy data, porosity data and fluid saturation data from the second wellbore to the rock physics model of i).

16. The method according to claim 1 wherein the subterranean rock formation surrounding the second wellbore is a conventional reservoir.

17. The method according to claim 1 wherein the subterranean rock formation surrounding the second wellbore is an unconventional reservoir.

18. The method according to claim 1 wherein the first wellbore is a vertical well.

19. The method according to claim 1 further comprising:
    v) determining mineralogy data by applying a mineralogy measurement process on cuttings gathered during a drilling process of a third wellbore; and
    vi) determining at least one elasticity property of the subterranean rock formation surrounding the third wellbore based at least in part on application of the mineralogy data determined in v) to the rock physics model of i); and
    vii) determining a minimum principal stress magnitude of the subterranean rock formation surrounding the third wellbore based at least in part on application of the at least one elasticity property determined in vi) to the geomechanical model of i).

20. The method according to claim 1 wherein the at least one elasticity property determined in iii) includes anisotropic elastic properties of the subterranean rock formation surrounding the second wellbore.

21. The method according to claim 1 wherein the determining of iii) and iv) is carried out during the drilling process of the second wellbore.

22. The method according to claim 1 wherein the determining of iii) and iv) is carried out after the drilling process of the second wellbore.

23. A system for determining subterranean properties comprising a processing system programmed and configured to:
    i) provide a rock physics model and a geomechanical model, wherein the rock physics model relates mineralogy data to at least one elasticity property, wherein the geomechanical model relates at least one elasticity property to minimum principal stress magnitude, and wherein at least the rock physics model is calibrated using measurements of a subterranean rock formation surrounding a first wellbore;

ii) determine mineralogy data by applying a mineralogy measurement process on cuttings gathered during a drilling process of a second wellbore;

iii) determine at least one elasticity property of the subterranean rock formation surrounding the second wellbore based at least in part on application of the mineralogy data determined in ii) to the rock physics model of i); and iv) determine a minimum principal stress magnitude of the subterranean rock formation surrounding the second wellbore based at least in part on application of the at least one elasticity property determined in iii) to the geomechanical model of i).

24. The system according to claim 23 wherein the measurements of the subterranean rock formation surrounding the first wellbore of i) include spectroscopy log data and multipole sonic log data from the first wellbore, and wherein the rock physics model of i) is calibrated by determining a subset of inorganic and organic mineralogy volume fractions using the spectroscopy log data, and determining a subset of a plurality of anisotropic elastic moduli using the multipole sonic log data.

25. The system according to claim 24 wherein the inorganic and organic mineralogy volume fractions are determined using knowledge of mineral densities and measurements of inorganic and organic mineralogy weight fractions.

26. The system according to claim 24 wherein the anisotropic elastic moduli are transversely isotropic.

27. The system according to claim 23 wherein the measurements of the subterranean rock formation surrounding the first wellbore of i) include mineralogy measurements and acoustic measurements made in a lab on core samples gathered from the first wellbore, and wherein the rock physics model of i) is calibrated by determining a subset of inorganic and organic mineralogy volume fractions using a mineralogy laboratory measurement device, and determining a subset of a plurality of anisotropic elastic moduli using an acoustic laboratory measurement device.

28. The system according to claim 23 wherein the mineralogy measurement process of ii) is of a type selected from or is a combination of one or more types selected from a group consisting of: Diffuse reflectance infrared Fourier transform spectroscopy (DRIFTS); Attenuated total reflectance (ATR); Laser-induced breakdown spectroscopy (LIBS); Fourier Transform Infrared (FTIR); FTIR+Laboratory Equipment Corporation method of estimating total organic carbon (LECO); X-Ray Fluorescence (XRF) Radial Basis Function (RBF); XRF RBF+LECO; X-ray diffraction (XRD); and XRD+LECO.

* * * * *